(12) United States Patent
Griebenow et al.

(10) Patent No.: US 7,887,978 B2
(45) Date of Patent: Feb. 15, 2011

(54) METHOD OF DETECTING REPEATING DEFECTS IN LITHOGRAPHY MASKS ON THE BASIS OF TEST SUBSTRATES EXPOSED UNDER VARYING CONDITIONS

(75) Inventors: Uwe Griebenow, Markkleeberg (DE); Martin Mazur, Pulsnitz (DE); Wolfram Grundke, Dresden (DE); Andre Poock, Malschwitz (DE)

(73) Assignee: GLOBALFOUNDRIES Inc., Grand Cayman (KY)

( * ) Notice: Subject to any disclaimer, the term of this patent is extended or adjusted under 35 U.S.C. 154(b) by 318 days.

(21) Appl. No.: 12/113,559

(22) Filed: May 1, 2008

(65) Prior Publication Data
US 2009/0274981 A1    Nov. 5, 2009

(30) Foreign Application Priority Data
Oct. 31, 2007    (DE) .................. 10 2007 052 052

(51) Int. Cl.
*G03F 9/00*    (2006.01)
(52) U.S. Cl. ............... 430/5; 430/30; 382/144
(58) Field of Classification Search .............. 430/5, 430/30; 382/144
See application file for complete search history.

(56) References Cited

U.S. PATENT DOCUMENTS 4,637,714 A    1/1987    Flamholz .................. 355/77

OTHER PUBLICATIONS

Jun. 26, 2008 letter from foreign associate forwarding Official Communication.
Translation of Official Communication issued May 19, 2008.

*Primary Examiner*—Christopher G Young
(74) *Attorney, Agent, or Firm*—Williams, Morgan & Amerson, P.C.

(57) ABSTRACT

Mask defects, such as crystal growth defects and the like, may be efficiently detected and estimated at an early stage of their development by generating test images of the mask under consideration and inspecting the images on the basis of wafer inspection techniques in order to identify repeatedly occurring defects. In some illustrative embodiments, the exposure process for generating the mask images may be performed on the basis of different exposure parameters, such as exposure doses, in order to enhance the probability of detecting defects and also estimating the effect thereof depending on the varying exposure parameters. Consequently, increased reliability may be achieved compared to conventional direct mask inspection techniques.

15 Claims, 5 Drawing Sheets

METHOD OF DETECTING REPEATING DEFECTS IN LITHOGRAPHY MASKS ON THE BASIS OF TEST SUBSTRATES EXPOSED UNDER VARYING CONDITIONS

BACKGROUND OF THE INVENTION

1. Field of the Invention

Generally, the subject matter disclosed herein relates to the manufacturing of integrated circuits, and, more particularly, to controlling defects during the formation of device features on the basis of advanced photolithography techniques using lithography masks.

2. Description of the Related Art

The fabrication of microstructures, such as integrated circuits, requires tiny regions of precisely controlled size to be formed in one or more material layers of an appropriate substrate, such as a silicon substrate, a silicon-on-insulator (SOI) substrate or other suitable carrier materials. These tiny regions of precisely controlled size are typically defined by patterning the material layer(s) by applying lithography, etch, implantation, deposition processes and the like, wherein, typically, at least in a certain stage of the patterning process, a mask layer may be formed over the material layer(s) to be treated to define these tiny regions. Generally, a mask layer may consist of or may be formed by means of a layer of photoresist that is patterned by a lithographic process, typically a photolithography process. During the photolithographic process, the resist may be spin-coated onto the substrate surface and then selectively exposed to radiation, typically ultraviolet radiation, through a corresponding lithography mask, such as a reticle, thereby imaging the reticle pattern into the resist layer to form a latent image therein. After developing the photoresist, depending on the type of resist, positive resist or negative resist, the exposed portions or the non-exposed portions are removed to form the required pattern in the layer of photoresist. Based on this resist pattern, actual device patterns may be formed by further manufacturing processes, such as etch, implantation, anneal processes and the like. Since the dimensions of the patterns in sophisticated integrated microstructure devices are steadily decreasing, the equipment used for patterning device features have to meet very stringent requirements with regard to resolution and overlay accuracy of the involved fabrication processes. In this respect, resolution is considered as a measure for specifying the consistent ability to print minimum size images under conditions of predefined manufacturing variations. One important factor in improving the resolution is represented by the lithographic process, in which patterns contained in the photomask or reticle are optically transferred to the substrate via an optical imaging system. Therefore, great efforts are made to steadily improve optical properties of the lithographic system, such as numerical aperture, depth of focus and wavelength of the light source used.

The resolution of the optical patterning process may therefore significantly depend on the imaging capability of the equipment used, the photoresist materials for the specified exposure wavelength and the target critical dimensions of the device features to be formed in the device level under consideration. For example, gate electrodes of field effect transistors, which represent an important component of modern logic devices, may be 50 nm and even less for currently produced devices with significantly reduced dimensions for device generations that are currently under development. Similarly, the line width of metal lines provided in the plurality of wiring levels or metallization layers may also have to be adapted to the reduced feature sizes in the device layer in order to account for the increased packing density. Consequently, the actual feature dimensions may be well below the wavelength of currently used light sources provided in current lithography systems. For example, currently in critical lithography steps, an exposure wavelength of 193 nm may be used, which therefore may require complex techniques for finally obtaining resist features having dimensions well below the exposure wavelength. Thus, highly non-linear processes are typically used to obtain dimensions below the optical resolution. For example, extremely non-linear photoresist materials may be used, in which a desired photochemical reaction may be initiated on the basis of a well-defined threshold so that weakly exposed areas may not substantially change at all, while areas having exceeded the threshold may exhibit a significant variation of their chemical stability with respect to a subsequent development process.

The usage of highly non-linear imaging processes may significantly extend the capability for enhancing the resolution for available lithography tools and resist materials.

Due to the complex interaction between the imaging system, the resist material and the corresponding pattern provided on the reticle even in highly sophisticated imaging techniques, which may possibly include optical proximity corrections (OPC), phase shifting masks and the like, the consistent printing of latent images, that is, of exposed resist portions which may be reliably removed or maintained, depending on the type of resist used, may also significantly depend on the specific characteristics of the respective features to be imaged. Furthermore, the respective process parameters in such a highly critical exposure process may have to be controlled to remain within extremely tight process tolerances, which may contribute to an increasing number of non-acceptable substrates, especially as highly scaled semiconductor devices are considered. Due to the nature of the lithography process, the corresponding process output may be monitored by respective inspection techniques in order to identify non-acceptable substrates, which may then be marked for reworking, that is, for removing the exposed resist layer and preparing the respective substrates for a further lithography cycle. However, lithography processes for complex integrated circuits may represent one of the most dominant cost factors of the entire process sequence, thereby requiring a highly efficient lithography strategy to maintain the number of substrates to be reworked as low as possible. Consequently, the situation during the formation of sophisticated integrated circuits may increasingly become critical with respect to throughput.

An important aspect in reducing failures associated with advanced lithography processes may be related to the photomasks or reticles that are used for forming the latent images in the resist layer of the substrates. In modern lithography techniques, typically an exposure field may be repeatedly imaged into the resist layer, wherein the exposure field may contain one or more die areas, the image of which is represented by the specific photomask or reticle. In this context, a reticle may be understood as a photomask in which the image pattern is provided in a magnified form and is then projected onto the substrate by means of an appropriate optical projection system. Thus, the same image pattern of the reticle may be projected multiple times onto the same substrate according to a specified exposure recipe, wherein, for each exposure process, the respective exposure parameters, such as exposure dose, depth of focus and the like, may be adjusted within a predetermined process window in order to obtain a required quality of the imaging process for each of the individual exposure fields. Thus, an exposure recipe may be defined by determining an allowable range of parameter values for each of the respective parameters, which may then be adjusted prior to the actual exposure process on the basis of appropriate data, such as an exposure map, and the like. Furthermore, prior to each exposure step, an appropriate alignment procedure may be performed to precisely adjust one device layer above the other on the basis of specified process margins.

During the entire exposure process, a plurality of effects may be created, which may be associated with any deficiencies or imperfections of the exposure tool, the substrate and the like. In this case, a plurality of defects may be generated, the occurrence of which may be systematic or random and may require respective tests and monitoring strategies. For example, a systematic drift of tool parameters of the exposure tools may be determined on the basis of regular test procedures, while substrate-specific defects may be determined on the basis of well-established wafer inspection techniques to locate respective defects, such as particles and the like. Another serious source of defects may be the photomask or reticle itself, due to particles on the reticle, damaged portions and the like. As previously explained, in sophisticated lithography techniques, a plurality of measures have to be implemented in order to increase the overall resolution, wherein, for instance, in many cases, phase shift masks may be used, which comprise portions with an appropriately defined optical length to obtain a desired degree of interference with radiation emanating from other portions of the reticle. For example, at an interface between a light-blocking region and a substantially transmissive region of the mask, respective diffraction effects may result in blurred boundaries, even for highly non-linear resist materials. In this case, a certain degree of destructive interference may be introduced, for instance, by generating a certain degree of phase shift of, for instance, 180 degrees, while also providing a reduced intensity of the phase shifted fraction of the radiation, which may result in enhanced boundaries in the latent image of the resist between resist areas corresponding to actually non-transmissive and transmissive portions in the photomask. Consequently, for certain types of reticles, a change of the absorption may result in a defect in the corresponding latent image in the resist layer, which may then be repeatedly created in each exposure field. Similarly, any other defects in the reticle may result in repeated defects, which may cause a significant yield loss if the corresponding defects may remain undetected over a certain time period. There are many reasons for failures caused by reticle defects, such as insufficiency of the manufacturing sequence for forming reticles, defects created during reticle transport and reticle handling activities and the like.

One class of reticle defects has recently drawn much attention, since the detection thereof, as well as temporal development of such defects, has not been very well understood. These defects mainly occur in connection with highly sophisticated lithography techniques using short wavelengths, such as 193 nm.

FIG. 1a schematically illustrates a cross-sectional view of a typical photomask or reticle, which may be used in sophisticated lithography techniques. The reticle 100 may comprise a substrate material 101, which may be substantially transparent for a specified exposure wavelength. For instance, quartz materials may frequently be used for lithography processes using deep UV radiation, since, in this case, the intrinsic absorption in this wavelength range may still be acceptable for transmissive optical components. The substrate material 101 may have formed specific non-transparent portions 102, which represent areas that are not to be exposed so as to become soluble or remain non-soluble, depending on the type of resist material used. For instance, the portions 102 may be formed of chromium, molybdenum silicide or any other appropriate material. As previously explained, the reticle 100 may represent a phase shift mask having areas 103 creating a specific shift in phase, while also possibly attenuating the incoming radiation to enhance the resolution of the optical imaging process, as explained above. A certain degree of phase shift may be created by providing the areas 103 with a specific optical thickness with respect to substantially transparent portions of the substrate material 101 in order to obtain a desired phase shift between the respective light beams passing through the portion 103 and transparent portions of the substrate 101. Furthermore, the reticle 100 may comprise a transparent polymer layer 104, which may also be referred to as a pellicle, that is provided with a certain distance to the pattern defined by the substrate material 101, the areas 103 and the features 102. Pellicles have been developed to protect the sensitive surface of reticles in view of defects, such as particles and scratches caused by reticle handling and the like. On the basis of the pellicle 104, the reticle 100 may be used in production over an extended lifetime compared to non-protected reticles, which may significantly contribute to a reduction of the overall production costs, since the manufacturing of reticles may be very expensive. For example, contamination of the pellicle 104 by particles during usage of the reticle 100 may not result in respective defects in the latent image created in the resist layer since the particles on the reticles may not be within the focal plane compared to the features 102 on the surface of the substrate material 101.

During an exposure process, the reticle 100 may be exposed to incoming radiation 105 of an appropriate wavelength range, which may pass through the reticle 100, thereby creating a beam 106 including a radiation pattern corresponding to the substrate material 101, the areas 103 and the features 102. As previously explained, a great number of exposure processes may be performed on the basis of a single reticle, until a general degradation may require the replacement of the reticle 100. With the introduction of DUV lithography processes, for instance using 193 nm, a specific type of reticle defect has emerged, which may not be prevented by the provision of the pellicle 104, or which may even be enhanced by the presence of the pellicle 104.

FIG. 1b schematically illustrates the reticle 100 after a plurality of exposure processes, thereby resulting in a defect 107, which may be referred to as a crystal growth defect, which may represent a photo-induced formation of a defect area, for instance, caused by out-gassing components of the pellicle 104 or any other components, such as adhesives and the like, or by components that may be present in the ambient of the reticle 100 during exposure. The defect 107 may thus "develop" over process time of the reticle 100 and may finally reach a stage in which a significant defect may also be created in the resist layer, thereby generating a repeating defect in the exposed substrates.

For this reason, sophisticated mask inspection techniques have been developed in order to identify respective defects creating repeating defects in product substrates on a regular basis to reduce the probability of causing a significant yield loss.

FIG. 1c schematically illustrates the reticle 100 according to a typical inspection technique. For this purpose, a light source, such as a laser 110, may direct light onto the reticle 100 on the basis of an appropriate optical system (not shown), while respective detectors 111 and 112 may detect the reflected part and the transmitted part of the initial incident light beam. Based on the corresponding signals of the detectors 111, 112, appropriate defect finding algorithms may be used in order to identify relevant defects in the reticle 100. For example, whenever a new reticle is obtained, a corresponding inspection test may be performed and may be repeated on a regular basis to monitor the degradation of the reticle 100. It turns out, however, that, for sophisticated photomasks, for instance comprising phase shift areas and the like, a reliable detection of defects, such as the crystal growth defect 107, is difficult, thereby requiring an increased frequency for the testing of the available reticles while only resulting in a moderately low probability for causing a repeating defect for a moderately large number of product substrates.

The present disclosure is directed to various methods that may avoid, or at least reduce, the effects of one or more of the problems identified above.

SUMMARY OF THE INVENTION

The following presents a simplified summary of the invention in order to provide a basic understanding of some aspects of the invention. This summary is not an exhaustive overview of the invention. It is not intended to identify key or critical elements of the invention or to delineate the scope of the invention. Its sole purpose is to present some concepts in a simplified form as a prelude to the more detailed description that is discussed later.

Generally, the subject matter disclosed herein relates to techniques for enhancing photolithography processes by improving the efficiency in estimating the printability of photolithography masks, such as reticles. That is, the principles disclosed herein provide enhanced techniques for estimating or identifying defects of reticles or photomasks at an early stage in the development of defects, such as crystal growth defects, even for complex photomasks, such as phase shift masks, by generating an image of the photomask under consideration on the basis of sophisticated exposure conditions, thereby increasing the sensitivity for detecting defects, which may otherwise remain undetected during regular exposure conditions or during regular mask inspections. Furthermore, using actually generated images for searching for defects on the photomask may provide an enhanced degree of authenticity of the entire imaging process, while also providing statistically relevant and meaningful measurement data which may be highly correlated to actual exposure processes.

One illustrative method disclosed herein relates to the detection of defects on a photolithography mask, wherein the method comprises performing a plurality of exposure processes with the photolithography mask on the basis of a first exposure parameter setting in order to generate a first plurality of images of the photolithography mask. The method further comprises performing a plurality of exposure processes with the photolithography mask on the basis of a second exposure parameter setting to generate a second plurality of images of the photolithography mask, wherein the first and second exposure parameter settings differ in at least one parameter value. Finally, the method comprises performing a defect inspection process on the first and the second pluralities of images to estimate the presence of a repeating defect in at least some of the first and second pluralities of images.

Another illustrative method disclosed herein comprises exposing a resist layer provided above a substrate by a lithography process using a specific photolithography mask and a first setting of exposure parameter values to generate a first plurality of images. At least one parameter value of the first setting is thereby outside of an allowable range that is applied, when the specific photolithography mask is used during the exposure of product substrates. Furthermore, the method comprises inspecting the first plurality of images to identify defects that repeatedly occur in the first plurality of images.

Another illustrative method disclosed herein relates to the estimation of printability of mask defects. The method comprises forming for each of a plurality of different process threads first images using a specific photolithography mask and a first setting of exposure parameters. Furthermore, second images are formed using the specific photolithography mask and a second setting of exposure parameters, wherein the first and second settings differ from each other. Additionally, the method comprises identifying defects repeatedly occurring in the first and second images associated with each of the different process threads. Finally, the printability of the repeatedly occurring defects of each of the different process threads is estimated on the basis of the first and the second images.

BRIEF DESCRIPTION OF THE DRAWINGS

The disclosure may be understood by reference to the following description taken in conjunction with the accompanying drawings, in which like reference numerals identify like elements, and in which.

Figure 1A:
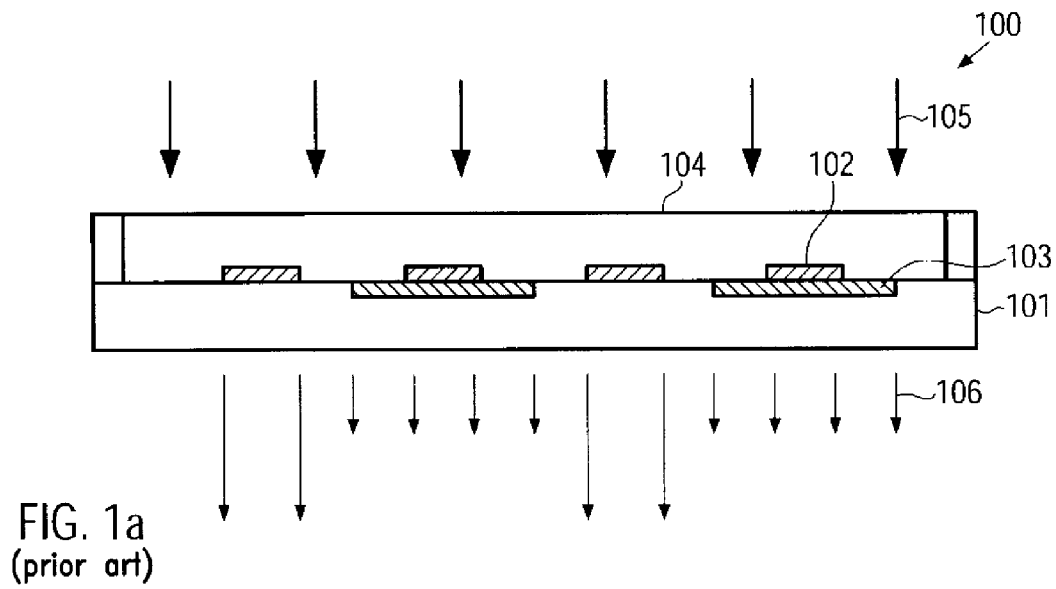
FIG. 1a schematically illustrates a cross-sectional view of a photomask during exposure.
Figure 1B:
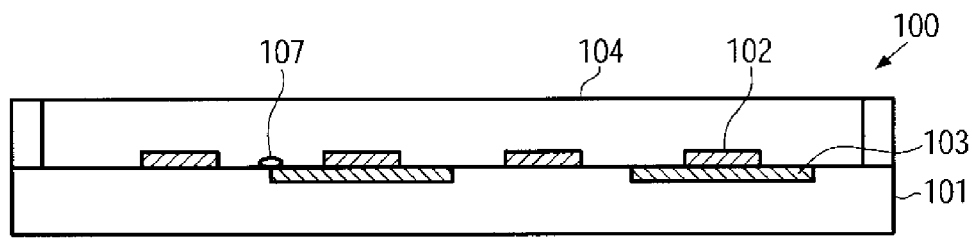
FIG. 1b schematically illustrates the photomask of FIG. 1a when comprising a defect, such a crystal growth defect.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures, systems and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Generally, the subject matter disclosed herein relates to process techniques for enhancing the efficiency in identifying defects on a photomask or reticle, even for highly complicated configurations, including phase shift masks and the like, wherein the development of respective defects may be identified in an early stage on the basis of actual images of the photomask under consideration. Thus, the actual defects or irregular areas of the photomask under consideration may be estimated on the basis of authentic conditions, thereby enabling the estimation of subtle effects, such as a change of phase shifting and the like, which may be difficult to estimate on the basis of inspection techniques using measurement data directly obtained from the photomask itself. Furthermore, in some illustrative aspects, appropriate exposure conditions may be used to allow the detection of respective irregular areas or defects on the photomask under consideration, which may substantially not affect the exposure process under regular exposure conditions, as may be used when exposing product substrates with the photomask under consideration. In this manner, a certain degree of predictability with respect to the occurrence of repeating defects under regular product conditions may be achieved, thereby enhancing the overall reliability of the manufacturing sequence. That is, upon identifying a corresponding defect in the photomask under consideration at an early development stage of the corresponding defect, such as a crystal growth defect, the printability, i.e., the possibility of further using the photomask, or the printability of the defects may be estimated in order to decide whether or not the photomask may be used for production, or when non-printability of the respective defect may be expected during the further utilization of the photomask, thereby providing valuable information for scheduling the process flow in the manufacturing environment. For example, the photomask under consideration may be tested on the basis of a reduced exposure dose, which may be outside of an allowable process range, in order to generate respective images, which may then be inspected in view of recognizing any repeating defects therein. A crystal growth defect may, therefore, be identified on the basis of a moderately low energy dose which under regular exposure conditions may not yet result in a critical defect, since a corresponding increased absorption or change of phase shift, or any other defect, may still be in a range that may result in acceptable lithography results. However, in this case, the position and other characteristics of the corresponding repeating defect may be determined and may be used for estimating the present and future printability of the defect, for instance on the basis of a respective threshold for a certain criterion, thereby achieving a certain degree of predictability for the further development of the defect under consideration. In other illustrative aspects, two or more different exposure settings may be used for the creation of the images to enhance the quantitative estimation of the printability of the defects or to enhance the detectability of defects. In some cases, two or more of the exposure settings used for the detection of defects may be outside of an allowable range to estimate the behavior of certain mask portions when "approaching" the allowable range of exposure parameter values from both sides. For example, when the exposure dose may be used as a variable process parameter value, an underexposed or overexposed image may be created for the photomask under consideration to more reliably estimate the effect of irregular mask portions on actual images in a resist layer.

In other illustrative aspects disclosed herein, an estimation of mask defects may be obtained with an increased resolution in terms of process flow related influences. That is, since the mask defects may be evaluated on the basis of actual images on substrates, other influences, such as the type of lithography tool used, any pre-exposure and/or post-exposure process tools and the like, may also be taken into consideration when evaluating the printability of respective mask defects. In particular, in highly complex mask configurations, for instance comprising OPC techniques, phase shift techniques and the like, the mutual interaction of a developing defect on a mask under consideration may relate to process thread dependent effects of the corresponding defect, possibly resulting in a different degree of "seriousness" of the defect under consideration depending on the process thread actually used, i.e., the combination of a specific reticle of interest with a plurality of possible tool combinations. Thus, in the case of a highly complex manufacturing environment, in which typically a plurality of lithography steps may be used, one and the same defect of a specific mask may also be classified with respect to different process flow categories, which may result in increased reliability for determining the printability of the defect under consideration.

Figure 2A:
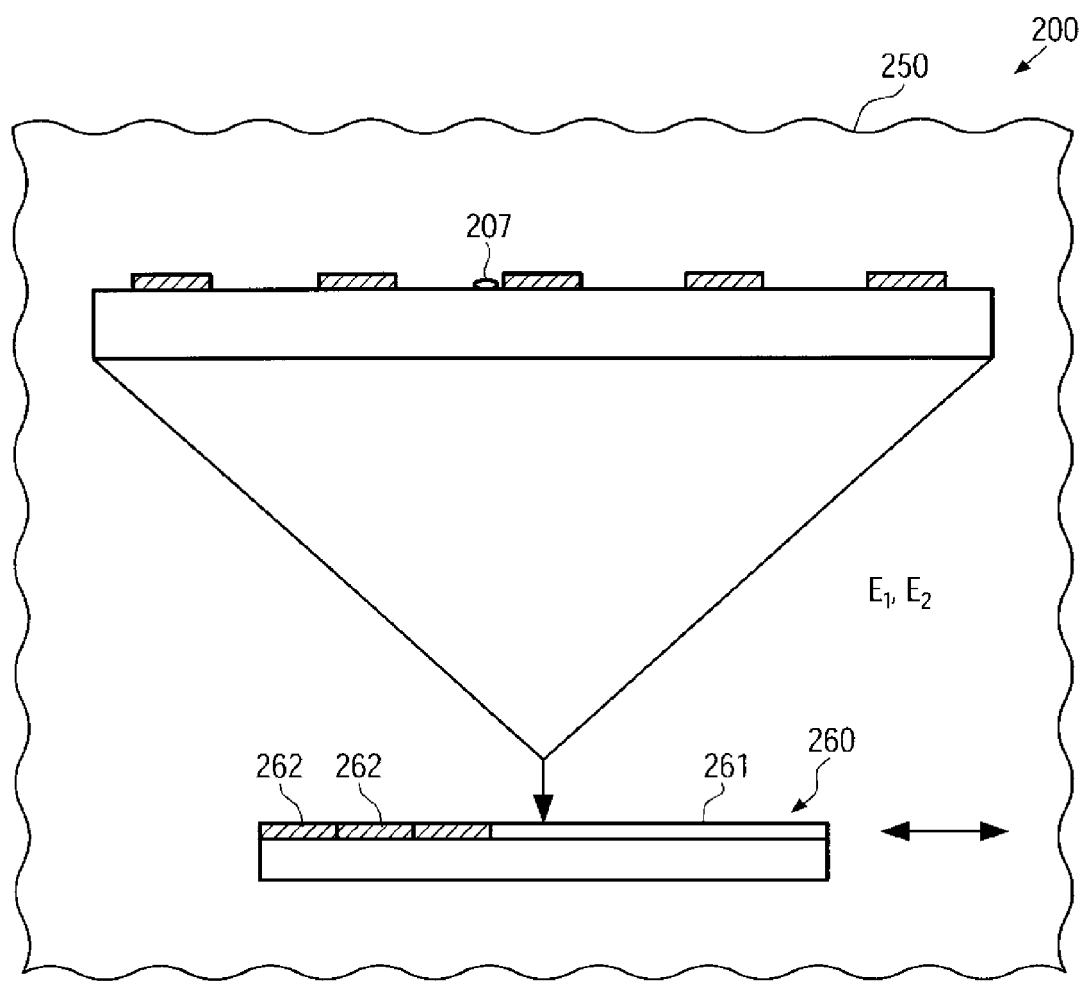
FIGS. 2a-2d schematically illustrate various concepts for testing a reticle with respect to repeating defects on the basis of images formed on a substrate according to illustrative embodiments.

FIG. 2a schematically illustrates a cross-sectional view of a lithography mask 200 that is to be considered a device under test in order to estimate or identify respective defects thereon, which may have been created during the manufacturing phase or during the storage or usage of the photomask 200, wherein respective defects may also be detected which may develop in relation to an accumulated radiation dose, such as photo-induced defects in the form of crystal growth defects, as previously explained. For example, the photomask 200 may have a similar configuration as previously described with respect to the photomask 100, that is, the mask 200 may represent any lithography mask comprised of transparent and substantially non-transparent portions, possibly in combination with radiation attenuating portions for attenuating and phase shifting an incident radiation, as previously explained with reference to the substrate material 101, the features 102 and the areas 103 of the photomask 100.

The photomask 200 may represent a corresponding pattern of a microstructure device corresponding to a specific device layer, wherein critical feature sizes may be in the range of several tenths of nm and even less in the device layer when, for instance, sophisticated CMOS semiconductor devices are considered, in which a gate length of transistors is in the range of approximately 50 nm and less. It should be appreciated that typically the mask 200 is to be considered as a reticle, that is, a template, in which the respective feature sizes are provided in a magnified form, for instance four or five times the size of the device features to be formed on a substrate. In this case, a lithography system, which is schematically indicated as 250, is configured to expose the mask 200 and project the image pattern onto a substrate 260 while appropriately reducing the size of the image pattern of the mask 200 by a complex optical system. In the embodiment shown, the substrate 260 may represent a dedicated test substrate having a substantially non-patterned surface, above which may be formed a resist layer 261, such as a positive resist or a negative resist, depending on the configuration of the mask 200.

Upon testing the mask 200, the lithography system 250 may be operated on the basis of a specified setting for exposure parameters, such as exposure dose, depth of focus and the like, in order to expose individual exposure fields 262 on the basis of respective parameter values. In some illustrative embodiments, the exposure process may be performed on the basis of process parameter values, for which at least one value is outside a regular range that may typically be used in exposure processes, when the photomask 200 is employed for exposing product substrates. That is, for typically respective exposure recipes for the device layer under consideration, i.e., a respective photomask in combination with a predetermined configuration of the resist layer and the like, a certain degree of variability of the parameter value may be allowed and may be desired in order to individually adjust the exposure conditions in each of the exposure fields 262 of substrates in such a manner that a high degree of uniformity of the finally obtained device features is obtained. Due to the fact that a plurality of exposure fields are provided across the entire substrate, the lithography process provides the possibility of enhancing the overall product uniformity by specifically adapting exposure parameters with respect to the position of a specific exposure field on the substrate. For example, if pre-exposure or post-exposure processes are known to provide a certain non-uniformity, an appropriate adaptation of process parameters, such as exposure dose, may provide the possibility of compensating, at least to a certain degree, for these non-uniformities. However, a variation of a respective process parameter value, such as the exposure dose, may not exceed certain limits and may have to stay within an allowable range for the specific lithography process, which is also referred to as a process window.

For instance, if a certain non-uniformity would require a high amount of radiation energy to be deposited on the specific exposure field, for instance, for reducing critical feature sizes, undue overexposure may, however, result in severe defects, for instance too thin gate lines and the like, which may not be compatible with the further processing of the device under consideration. Similarly, significant underexposure may also result in non-acceptable device features. Thus, in one illustrative embodiment, the at least one parameter value, such as the exposure dose, i.e., amount of energy deposited by the exposure process, may be selected to be outside of the allowable range in order to enable the estimation of possible defects, such as a defect 207, on the basis of process conditions, which may not occur during a regular production process. Thus, the effect of the defect 207 may be estimated in a stage in which, under regular exposure conditions, the defect 207 would possibly not result in significant defects on a product. In this case, the defect 207 would be considered as a printable defect, since the mask 200 would further be available for production. In some illustrative aspects, the at least one process parameter, such as the exposure dose, may be varied to obtain a plurality of exposure fields 262 on the basis of a first parameter value while also obtaining a plurality of exposure fields 262 on the basis of a second different value, wherein, in some embodiments, the second value may also be outside the allowable parameter value range. Hence, defects may be identified under process conditions corresponding to the size of the allowable parameter value range, while still not significantly affecting the exposure process under production conditions.

Figure 2B:
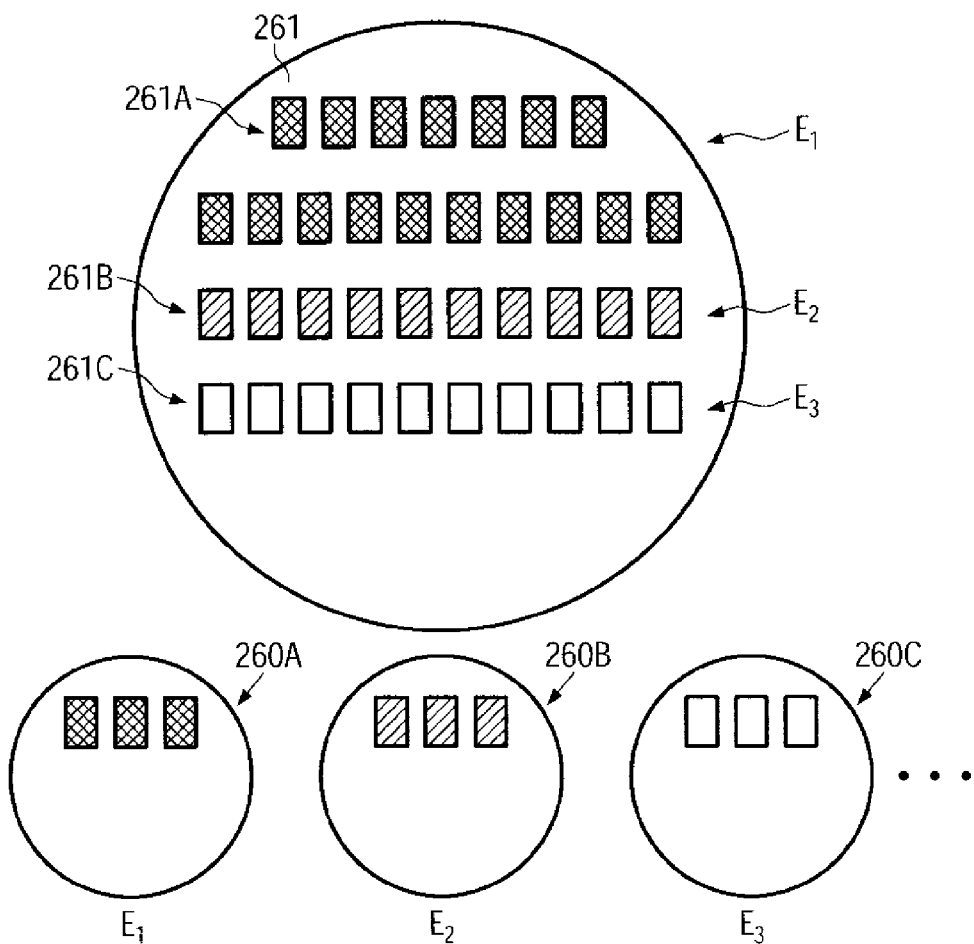

FIG. 2b schematically illustrates a top view of one or more test substrates 260, which may have formed thereon a plurality of images or exposure fields 261 which may be obtained on the basis of different parameter values, such as different exposure doses, depth of focus and the like. For instance, in the embodiment shown, the substrate 260 may comprise a plurality of images 261 obtained on the basis of a plurality of different exposure doses $E_1$, $E_2$, $E_3$. In the embodiment shown, the exposure fields or images 261 may be formed on a single substrate, wherein each of the pluralities of images 261A, 261B, 261C may be provided with a sufficient number of individual images in order to obtain statistically relevant statements when analyzing each of the plurality of images 261A, 261B, 261C in view of repeatedly occurring defects, which may therefore stem from a respective defect of the mask 200, such as the defect 207.

In other illustrative embodiments, respective dedicated test substrates 260A, 260B, 260C may be used, wherein each of the substrates 260A, 260B, 260C may comprise respective images 261 formed on the basis of a different parameter value, such as a different exposure dose. In this case, each parameter value may be examined with high statistical relevance, wherein different parameter values may also be compared with each other on the basis of identical conditions with respect to the position of exposure fields on the respective test substrates 260A, 260B, 260C.

Figure 2C:
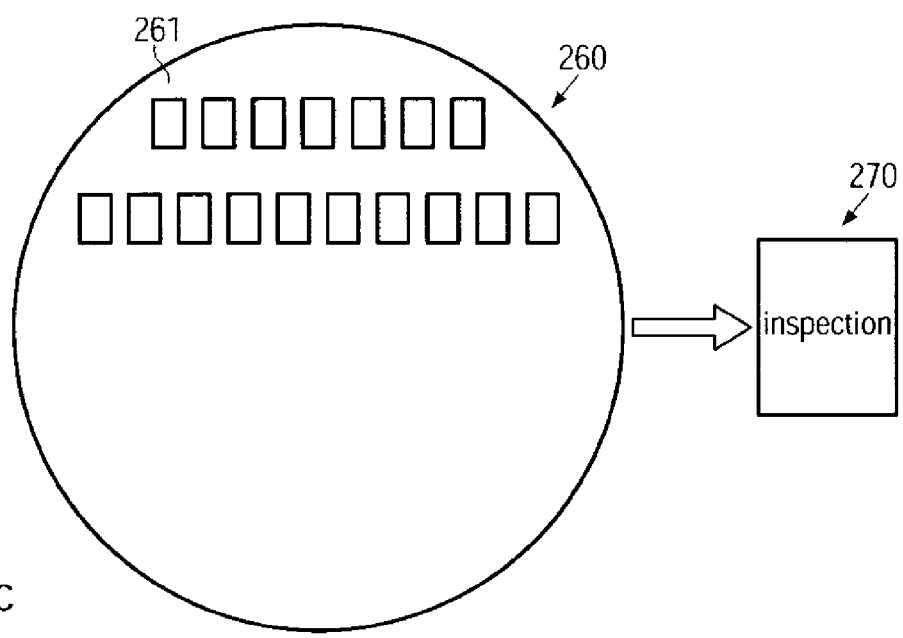

FIG. 2c schematically illustrates one of the test substrates 260 when subjected to an inspection process, which may be performed on the basis of any appropriate defect inspection system 270, which may be configured for efficiently identifying defects in the exposure fields 261. For example, sophisticated inspection tools 270 and respective defect recognition algorithms are available in the art and may be used for this purpose.

Figure 2D:
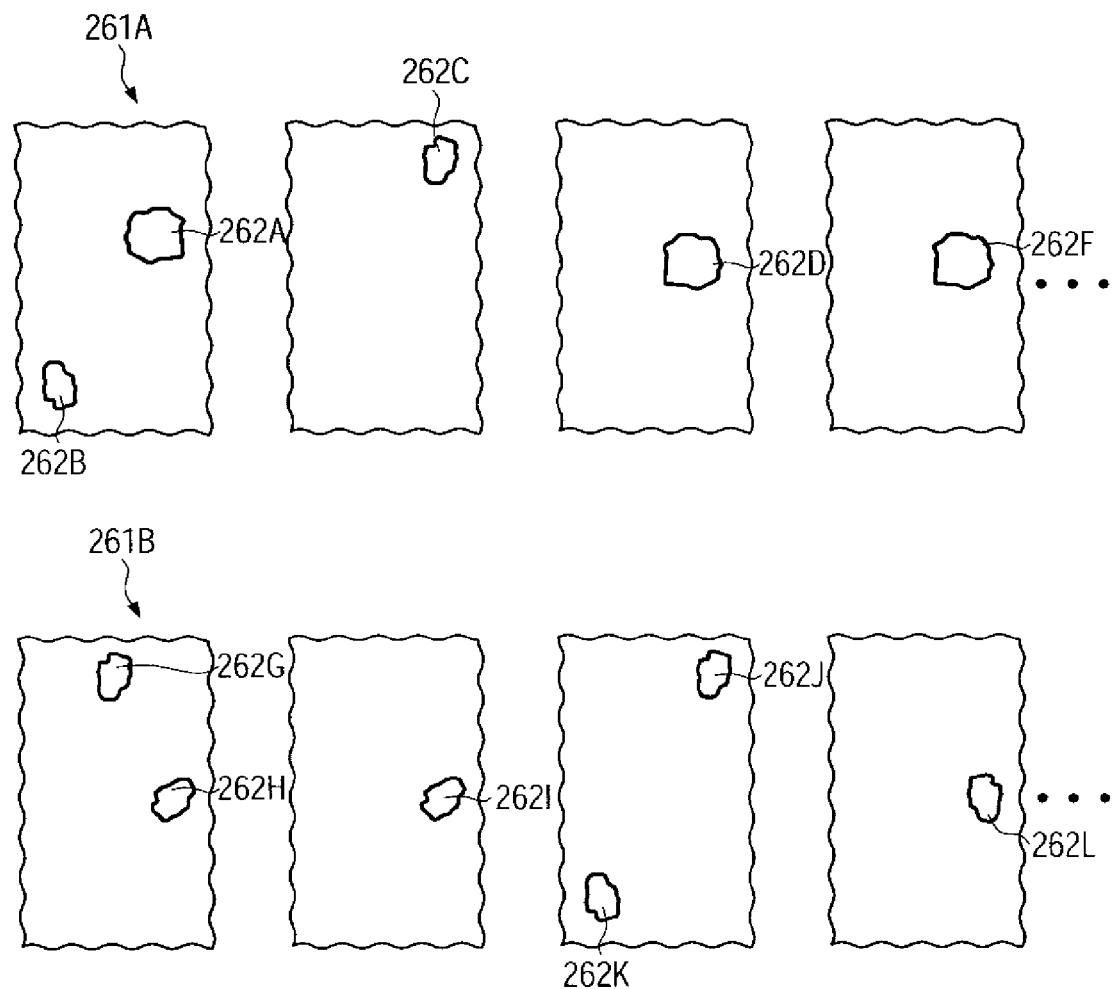

FIG. 2d schematically illustrates a possible inspection process performed in the inspection system 270, for instance, on the basis of optical techniques to identify defects in the exposure fields 261. As shown, certain defects 262A-262L may be identified by the inspection tool 270, for instance, by sophisticated image recognition techniques for detecting any abnormalities in the images 261. In the example shown, a first defect 262A may have been identified in a certain portion of the image 261A, which may have a certain lateral size and a position as determined by the inspection tool 270. For instance, the lateral size of the defect 262A may be in a range of several hundred nanometers to several micrometers. For instance, the defect 262A may correspond to a region having obtained a reduced amount of radiation energy during the exposure process performed on the basis of the mask 200. It may be assumed that, in the portion shown, the defect 262B may also be identified by the inspection system 270, for instance, with different coordinates and a different lateral size. Similarly, defects 262D, 262E, 262F may be identified in other regions 261, wherein, for instance, the coordinates of the defects 262D, 262F may substantially coincide with the coordinates of the defect 262A, thereby indicating a high probability that the defects 262A, 262D and 262F may have been created by a defect of the mask 200. Since the images 261A may be provided with a sufficient number, a corresponding probability may be determined with high statistical relevance which may allow identifying a repeatedly occurring defect with high confidence, thereby enabling the identification of a defect of the mask 200.

Similarly, the images 261B, which may have been created on the basis of a different parameter value, such as a different exposure dose, may also be evaluated in order to determine a repeatedly occurring defect in the images 261B. For instance, respective defects 262H, 262I and 262L may correspond in position to each other and may indicate the presence of a repeatedly occurring defect, which may be caused with high probability by a defect of the mask 200. In the example shown, the defects 262H, 262I and 262L may also correspond in coordinates to the defects 262A, 262D, 262F, thereby indicating that these defects are caused by one and the same defect on the mask 200. Moreover, in this case, the defect on the mask 200, such as the defect 207, may be estimated on the basis of different exposure conditions, which may enable an estimation of the printability of the defect 207 for upcoming production processes.

Figure 1C:
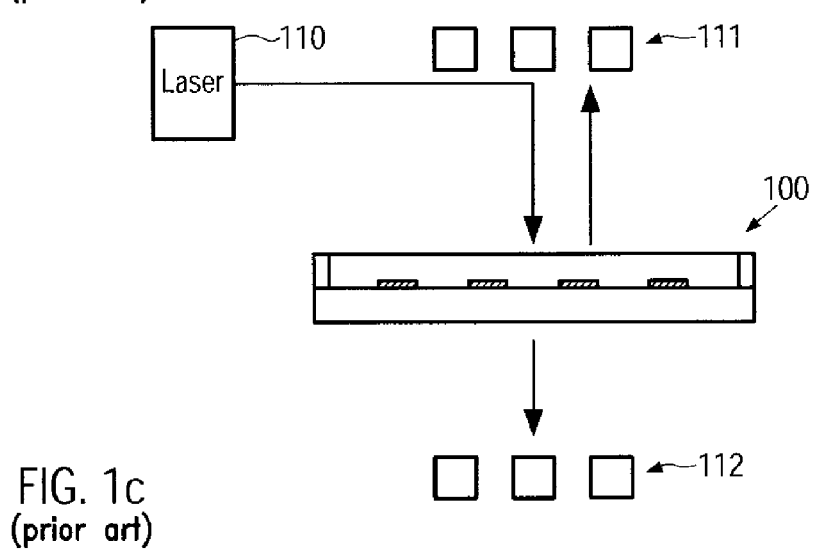
FIG. 1c schematically illustrates a conventional test regime for identifying defects on a photolithography mask.

For instance, the defect 207 may result in only minor distortions on actual devices when exposed on the basis of an allowable exposure dose range, where a value below the allowable range may correspond to the defects 262H, 262I, 262L, while the effect of the upper limit of the allowable range may correspond to the defects 262A, 262D, 262F. In this case, a strong dependence of the defect on the parameter value may indicate that a similar strong dependence of the defect on the further "development" of the defect may be expected. For example, the defect 207 may be located within a phase shifting area of the mask 200, which may result in a significant dependence of the effect of the defect 207 on actual image features in the printed images 261A, 261B. However, a corresponding haze or crystal growth defect may not be efficiently detected by direct mask inspection techniques, as for instance described with reference to FIG. 1c, since a change of transmission across a specific area of a phase shifting area of the mask 200 may not result in a pronounced signal directly obtained from the mask 200 when subjected to a process as described in FIG. 1c. Thus, since a respective defect 207 may presently result in an acceptable image distortion, which may remain undetected in actual product substrates, the presence and the further development of the defect 207 may remain undetected according to conventional techniques. On the other hand, using a plurality of different parameter values in combination with an actual exposure process provides a high degree of probability to detect the defect 207 even at an early stage of its development, so that enhanced overall process robustness may be achieved, while additionally the identification of a dependence on the process parameter value may allow estimation of a quantitative indication on the further development and thus printability of the defect 207.

Figure 2E:
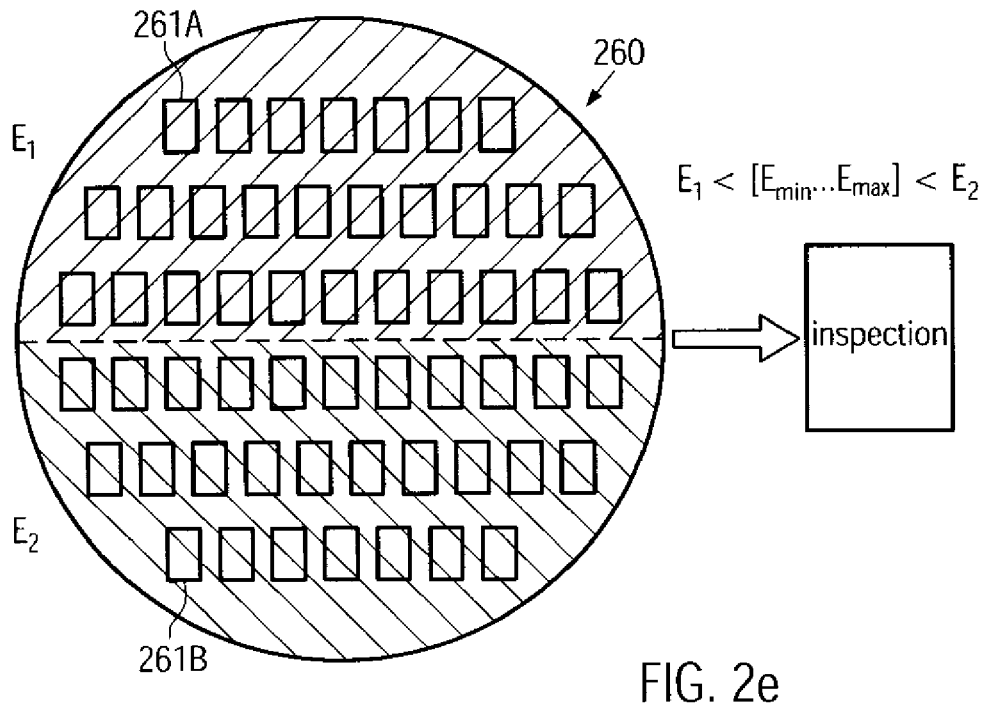
FIG. 2e schematically illustrates portions of images for identifying repeating defects of a photomask according to further illustrative embodiments.

FIG. 2e schematically illustrates the test substrate 260 according to a further illustrative embodiment, which may comprise the images or exposure fields 261A on one half of the substrate 260, and which may have been exposed by an exposure dose $E_1$ that is lower than a minimum exposure dose of an allowable range, while the other half of the substrate 260 may comprise images 261B obtained on the basis of an exposure dose that is higher than a maximum exposure dose of the allowable exposure range. Thus, in this case, images for two representative parameter values may be obtained on a single substrate, thereby providing high statistical relevance of the respective inspection data while also not unduly contributing to overall process time for obtaining the inspection measurement data.

Figure 2F:
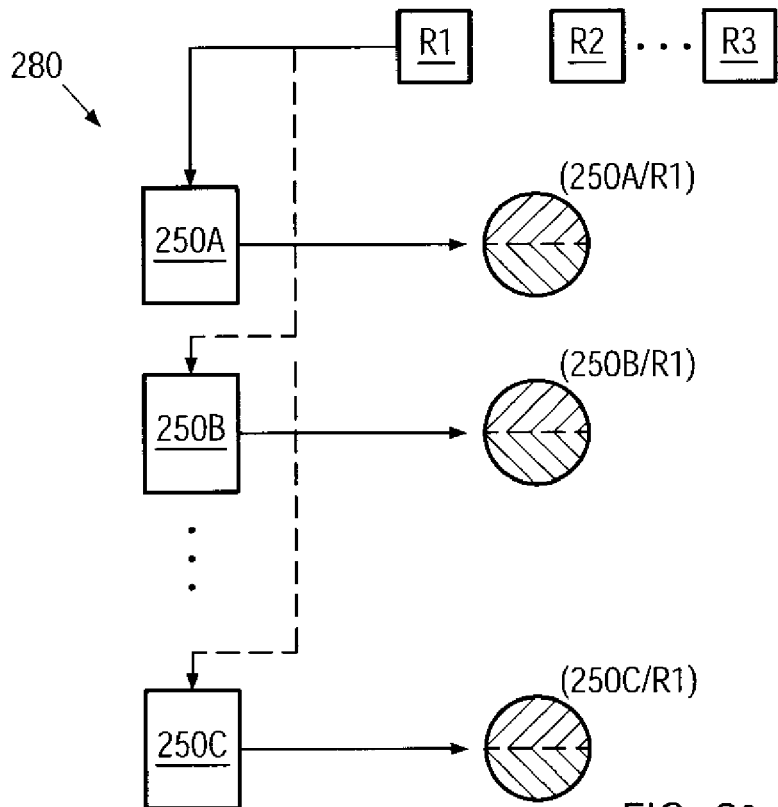
FIG. 2f schematically illustrates a manufacturing environment including a plurality of process threads or paths, in which a specific reticle may be used, wherein each possible process thread may be tested with respect to the occurrence of repeating defects of the specific photomask, according to still further illustrative embodiments.

FIG. 2f schematically illustrates a manufacturing environment 280 including a plurality of exposure tools 250A, 250B, 250C, which may be operated on the basis of a plurality of reticles R1, R2, R3. The reticles R1, R2, R3, may represent reticles representing the same device layer and thus may comprise identical images corresponding to the device layer under consideration. Thus, for each of the reticles R1, R2, R3, different process threads may occur during the production, since the reticles R1, R2, R3 and the lithography tools 250A, 250B and 250C may be temporarily associated with each other in accordance with the status of the manufacturing environment 280. For instance, some of the reticles R1, R2, R3 may not be available during certain phases of the manufacturing process and, similarly, the availability of the lithography tools 250A, 250B, 250C may change over time. Consequently, for instance, the reticle R1 may be used in combination with different process tools during different time periods, wherein a similar variability in respective post-exposure and pre-exposure process tools may also occur. When, for instance, the photomask R1 is to be tested in view of defects, respective test substrates may be obtained on the basis of a plurality of different process threads, i.e., on the basis of different combinations of reticles and exposure tools, possibly in combination with other pre- and post-exposure tools. In the example shown, one or more test substrates may be obtained for the mask R1 in combination with the tool 250A, for the mask R1 in combination with the tool 250B and for the mask R1 in combination with the tool 250C, which may then be subjected to an inspection process, as previously explained with reference to FIGS. 2c-2d. Consequently, for each process thread (250A/R1), (250B/R1), (250C/R1), respective inspection data may be analyzed in order to identify and estimate the presence of repeated defects. It should be appreciated that, due to subtle differences in the respective process threads, a different assessment of respective defects may occur, wherein, possibly in some assessed threads, no defects may be identified at all, while, in other assessed threads, defects may be determined, wherein the effect of a corresponding defect in the mask R1 may be more or less pronounced depending on the process thread under consideration.

Based on the inspection data obtained based on the images 261, the printability of the mask 200 or R1 may be estimated, for instance, by defining an appropriate threshold for one or more defect criteria, such as a lateral size of a defect determined in the images 261, a difference in lateral size of defects obtained on the basis of two different values of an exposure parameter and the like. The threshold value may indicate the printability and may therefore indicate whether or not the mask 200 or R1 may further be used in the production. Moreover, in other cases, a plurality of different threshold values may be determined in advance, for instance, in view of the above-identified criteria, to obtain a certain quantitative assessment with respect to the future development and thus of the usability of the mask 200 or R1 with respect to a certain time horizon. For instance, if a specified threshold may not be exceeded by the presently obtained inspection data, it may be indicated that the defect under consideration may remain uncritical in the near future and thus the corresponding photomask may be used without any restrictions. In other cases, exceeding a threshold may indicate that the defect is approaching a critical size and may require more frequent inspections compared to a mask corresponding to a lower threshold. Furthermore, when a plurality of defects are identified, the most critical defect may determine a corresponding "defect class" of the photomask under consideration so that the probability of creating severe defects on product substrates is maintained at a low level for the most serious detected defect.

As a result, the subject matter disclosed herein provides an enhanced technique for identifying and estimating defects on photomasks with increased reliability compared to conventional techniques by actually generating a plurality of images and subjecting the images to an inspection process for identifying repeatedly occurring defects therein. In some illustrative aspects, process parameters may be used during the exposure of the photomask, which may allow the evaluation of defects under extreme conditions, such as a reduced exposure dose and/or an increased exposure dose with respect to an allowable exposure dose range, thereby providing the possibility of studying the effects of possible defects outside the actual process window. Thus, the development of defects, such as crystal growth defects, may be detected at an early development stage, even for complex photomasks, such as phase shift masks, thereby reducing the occurrence of severe defects in product substrates. For example, conventional strategies using a direct inspection of photomasks, as is described for instance with reference to FIG. 1c, may be efficiently combined with the techniques disclosed herein, thereby further enhancing the overall reliability of the defect detection process. In some illustrative embodiments, a direct mask inspection may be efficiently combined with the above-described strategies to estimate the defect revealed by the conventional test strategy. That is, respective defects may be identified by a direct mask inspection and the printability of these defects may be estimated on the basis of the strategy described above, thereby obtaining a quantitative assessment about whether or not a photomask under consideration is further employable in production processes. The provision of respective measurement data of a direct mask inspection may significantly enhance the inspection process on the substrate level since appropriate coordinates of defects may be available and may be used in immediately identifying respective regions in the actual images. In some illustrative embodiments, the direct mask inspection may be combined with a complete image inspection to obtain a full overview with respect to any defect of a mask under consideration, since defects that may not be detected by the direct mask inspection may be revealed by the image inspection, while, on the other hand, defects indicated by the direct mask inspection might be estimated in view of their actual effect on the substrate level by the image inspection and the associated assessment, as described above.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method of detecting defects on a photolithography mask, the method comprising:

performing a plurality of exposure processes with said photolithography mask on the basis of a first exposure parameter setting to generate a first plurality of images of said photolithography mask, wherein said first exposure parameter setting is selected to be outside a range of allowable parameter values for exposure parameters when using said photolithography mask during production, said first exposure parameter setting being above said range;

performing a plurality of exposure processes with said photolithography mask on the basis of a second exposure parameter setting to generate a second plurality of images of said photolithography mask, wherein said second exposure parameter setting is selected to be outside said range, said second exposure parameter setting being below said range; and performing a defect inspection process on said first and second pluralities of images to determine the presence of a repeating defect in at least some of said first and second pluralities of images.

2. The method of claim 1, wherein said at least one parameter value differing in said first and second exposure parameter setting is an exposure dose.

3. The method of claim 1, wherein said first and second plurality of images are generated on a single substrate.

4. The method of claim 1, wherein said photolithography mask is a mask including attenuating areas to generate a phase shift with respect to non-attenuating areas.

5. The method of claim 1, further comprising determining a printability of a detected defect on the basis of said first and second pluralities of images.

6. The method of claim 5, wherein determining said printability comprises determining a threshold for at least one image feature of said first and second pluralities of images.

7. The method of claim 1, further comprising detecting preliminary defects on said photolithography mask by inspecting said photolithography mask and determining printability of said preliminary defects on the basis of said first and second pluralities of images formed on one or more test substrates.

8. A method, comprising:

exposing a resist layer provided above a substrate by a lithography process using a specific photolithography mask and a first setting of exposure parameter values to generate a first plurality of images, at least one parameter value of said first setting being above an allowable range applied when using said specific photolithography mask during exposure of product substrates;

generating a second plurality of images using said specific photolithography mask and a second setting of exposure parameters, said at least one parameter value in said second setting being below said allowable range; and comparing said first and second pluralities of images to identify defects that repeatedly occur in said first plurality of images.

9. The method of claim 8, wherein said at least one parameter value represents an exposure dose.

10. The method of claim 8, wherein said first and second pluralities of images are formed in said resist layer of said substrate.

11. The method of claim 8, wherein said first and second pluralities of images are formed above different substrates.

12. The method of claim 8, further comprising estimating a printability of a repeating defect on the basis of said first and second pluralities of images.

13. A method of estimating printability of mask defects, the method comprising:

forming for each of a plurality of different process threads first images using a specific photolithography mask and a first setting of exposure parameters above an allowable range used for processing product substrates in said plurality of different process threads and second images using said specific photolithography mask and a second setting of exposure parameters below said allowable range;

identifying defects repeatedly occurring in said first and second images associated with each of said different process threads; and determining printability of said repeatedly occurring defects of each of said different process threads on the basis of said first and second images.

14. The method of claim 13, wherein said first and second images of a specific process thread are formed on a common substrate.

15. The method of claim 13, wherein said first and second settings differ from each other in at least an exposure dose.

* * * * *